US009956273B2

(12) United States Patent
Gruskin et al.

(10) Patent No.: US 9,956,273 B2
(45) Date of Patent: *May 1, 2018

(54) COMPOSITIONS AND METHODS FOR PROMOTING NEURONAL OUTGROWTH

(71) Applicant: Acorda Therapeutics, Inc., Ardsley, NY (US)

(72) Inventors: Elliott A. Gruskin, Malvern, PA (US); Jennifer F. Iaci, Boonton, NJ (US); Andrea M. Vecchione, Mount Vernon, NY (US); Sarah J. Kasperbauer, Cortlandt Manor, NY (US); Gargi Roy, Boyds, MD (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/179,178

(22) Filed: Jun. 10, 2016

(65) Prior Publication Data
US 2016/0279210 A1    Sep. 29, 2016

Related U.S. Application Data

(63) Continuation of application No. 14/317,106, filed on Jun. 27, 2014, now Pat. No. 9,468,671, which is a continuation of application No. 13/451,968, filed on Apr. 20, 2012, now Pat. No. 8,785,606, which is a continuation of application No. 10/513,573, filed as application No. PCT/US03/14156 on May 5, 2003, now Pat. No. 8,183,350.

(60) Provisional application No. 60/377,669, filed on May 4, 2002.

(51) Int. Cl.
*A61K 38/48* (2006.01)
*A61K 31/726* (2006.01)
*A61K 31/737* (2006.01)
*A61K 38/51* (2006.01)
*C12N 9/88* (2006.01)

(52) U.S. Cl.
CPC ................ *A61K 38/51* (2013.01); *C12N 9/88* (2013.01); *C12Y 402/02005* (2013.01); *C12Y 402/02019* (2013.01)

(58) Field of Classification Search
None
See application file for complete search history.

(56) References Cited

U.S. PATENT DOCUMENTS

| 5,262,522 A | 11/1993 | Gearing |
| 5,270,194 A | 12/1993 | D'Alterio et al. |
| 5,496,718 A | 3/1996 | Hashimoto |
| 5,498,536 A | 3/1996 | Khandke |
| 5,578,480 A | 11/1996 | Khandke |
| 5,652,122 A | 7/1997 | Frankel et al. |
| 5,670,617 A | 9/1997 | Frankel et al. |
| 5,674,980 A | 10/1997 | Frankel et al. |
| 5,747,641 A | 5/1998 | Frankel et al. |
| 5,763,205 A | 6/1998 | Hashimoto et al. |
| 5,792,743 A | 8/1998 | Schachner |
| 5,804,604 A | 9/1998 | Frankel et al. |
| 5,869,301 A | 2/1999 | Nghiem et al. |
| 5,997,863 A | 12/1999 | Zimmerman et al. |
| 6,007,810 A | 12/1999 | Ishikawa et al. |
| 6,063,378 A | 5/2000 | Nohara et al. |
| 6,093,563 A | 7/2000 | Bennett et al. |
| 6,153,187 A | 11/2000 | Yacoby-Zeevi |
| 6,171,575 B1 | 1/2001 | Okuyama |
| 6,184,023 B1 | 2/2001 | Hashimoto et al. |
| 6,200,564 B1 | 3/2001 | Lamont et al. |
| 6,248,562 B1 | 6/2001 | Dunn et al. |
| 6,254,870 B1 | 7/2001 | Staten et al. |
| 6,313,265 B1 | 11/2001 | Phillips et al. |
| 6,326,166 B1 | 12/2001 | Pomerantz et al. |
| 6,972,168 B2 | 8/2005 | Muir et al. |
| 7,008,783 B1 | 3/2006 | Sato et al. |
| 7,074,581 B2 | 7/2006 | Yamashita et al. |
| 7,163,545 B2 | 1/2007 | Yaszemski et al. |
| 7,465,705 B2 | 12/2008 | Lee et al. |
| 7,507,570 B2 | 3/2009 | Prabhakar et al. |
| 7,560,106 B2 | 7/2009 | Sasisekharan et al. |
| 2003/0040112 A1 | 2/2003 | Muir et al. |
| 2003/0072749 A1 | 4/2003 | Muir et al. |
| 2003/0077258 A1 | 4/2003 | Muir |
| 2004/0033221 A1 | 2/2004 | Masuda et al. |
| 2004/0265297 A1 | 12/2004 | Gruskin et al. |
| 2005/0118157 A1 | 6/2005 | McMahon et al. |

(Continued)

FOREIGN PATENT DOCUMENTS

| AU | 2003/208466 B2 | 9/2003 |
| AU | 2003/265561 A1 | 3/2004 |
| AU | 2004/241088 A1 | 12/2004 |
| AU | 2004/0247025 B8 | 10/2011 |
| AU | 2006/294755 B2 | 4/2012 |
| CA | 2071898 A1 | 4/1991 |

(Continued)

OTHER PUBLICATIONS

Tkalec et al. "Isolation and Expression in *Escherichia coli* ofcslA and cslB, Genes Coding for the Chondroitin Sulfate-Degrading Enzymes Chondroitinase AC and Chondroitinase B, Respectively, From Flavobacterium Heparinum" (2000) Appl. Environ. Microbial. 66(1):29-35.

(Continued)

*Primary Examiner* — Kimberly Ballard
*Assistant Examiner* — Stacey N MacFarlane
(74) *Attorney, Agent, or Firm* — Pepper Hamilton LLP

(57) ABSTRACT

Neural outgrowth in the central nervous system is achieved by administering chondroitinase AC and/or chondroitinase B to degrade chondroitin sulfate proteoglycans that inhibit or contribute to the inhibition of nervous tissue regeneration.

10 Claims, No Drawings

(56) References Cited

U.S. PATENT DOCUMENTS

| | | |
|---|---|---|
| 2005/0233419 A1 | 10/2005 | Pojasek et al. |
| 2006/0078959 A1 | 4/2006 | Prabhaker et al. |
| 2006/0153827 A1 | 7/2006 | Gruskin et al. |
| 2006/0233782 A1 | 10/2006 | Gruskin et al. |
| 2007/0104703 A1 | 5/2007 | Caggiano et al. |
| 2007/0274979 A1 | 11/2007 | Gruskin et al. |
| 2009/0060895 A1 | 3/2009 | Caggiano et al. |
| 2011/0250631 A1 | 10/2011 | Gruskin et al. |
| 2011/0262413 A1 | 10/2011 | Gruskin et al. |
| 2012/0207732 A1 | 8/2012 | Gruskin et al. |
| 2012/0308571 A1 | 12/2012 | Caggiano et al. |
| 2013/0210082 A1 | 8/2013 | Caggiano et al. |
| 2013/0243765 A1 | 9/2013 | Gruskin et al. |
| 2014/0193387 A1 | 7/2014 | Gruskin et al. |
| 2014/0248253 A1 | 9/2014 | Gruskin et al. |
| 2014/0322192 A1 | 10/2014 | Gruskin et al. |
| 2015/0023942 A1 | 1/2015 | Gruskin et al. |
| 2015/0190483 A1 | 7/2015 | Caggiano et al. |
| 2015/0299687 A1 | 10/2015 | Grukskin et al. |

FOREIGN PATENT DOCUMENTS

| | | |
|---|---|---|
| CA | 2364690 A1 | 10/2000 |
| CA | 2455827 A1 | 2/2003 |
| CA | 2623635 C | 4/2013 |
| EP | 0704532 A2 | 4/1996 |
| EP | 1631234 A2 | 3/2006 |
| EP | 1646353 A2 | 4/2006 |
| EP | 2353606 A2 | 8/2011 |
| EP | 2354155 A2 | 8/2011 |
| JP | H10-174598 | 6/1998 |
| JP | 2004-113166 | 4/2004 |
| WO | WO 1991/06303 A | 5/1991 |
| WO | WO 1994/25567 A1 | 11/1994 |
| WO | WO 1995/13091 A1 | 5/1995 |
| WO | WO 1995/14478 A1 | 6/1995 |
| WO | WO 1996/01894 A1 | 1/1996 |
| WO | WO 1999/46364 | 9/1999 |
| WO | WO 1999/46368 A2 | 9/1999 |
| WO | WO 2000/52149 A1 | 9/2000 |
| WO | WO 2000/59942 A2 | 10/2000 |
| WO | WO 2000/62067 A1 | 10/2000 |
| WO | WO 2000/64482 A1 | 11/2000 |
| WO | WO 2000/075319 A1 | 12/2000 |
| WO | WO 2001/39795 A2 | 6/2001 |
| WO | WO 2002/08285 A2 | 1/2002 |
| WO | WO 2002/055684 A | 7/2002 |
| WO | WO 2002/65136 A2 | 8/2002 |
| WO | WO 2002/083179 A2 | 10/2002 |
| WO | WO 2003/000901 A2 | 1/2003 |
| WO | WO 2003/015612 A2 | 2/2003 |
| WO | WO 2003/22882 A2 | 3/2003 |
| WO | WO 2003/31578 A2 | 4/2003 |
| WO | WO 2003/074080 A1 | 9/2003 |
| WO | WO 2003/100031 A2 | 12/2003 |
| WO | WO 2003/102160 A2 | 12/2003 |
| WO | WO 2004/017044 A2 | 2/2004 |
| WO | WO 2004/103299 A2 | 12/2004 |
| WO | WO 2004/108069 A2 | 12/2004 |
| WO | WO 2004/110359 A2 | 12/2004 |
| WO | WO 2004/110360 A2 | 12/2004 |
| WO | WO 2005/112986 A2 | 12/2004 |
| WO | WO 2005/087920 A2 | 9/2005 |
| WO | WO 2007/038548 A2 | 4/2007 |
| WO | WO 2008/045970 A2 | 4/2008 |

OTHER PUBLICATIONS

Accession P59807, Aug. 15, 2003 UniProtKB/Swiss-Prot.
Aldrich "Enzymer Explorer" 2009, URL: http://www.sigmaaldrich.com/life-science/metabolomics/enzyme-explorer/learning-center/carbohydrate-analysis/carbohydrate-analysis-iii.
Anderson et al. "Tumor Cell Retention of Antibody Fab Fragments is Enhanced by an Attached HIV TAT Protein-Derived Peptide" 1993, Biochem. & Biophys. Res. Commun. 194(2):876-884.
Appel et al. "Several Extracellular Domains of the Neural Cell Adhesion Molecule L1 are Involved in Neurite Outgrowth and Cell Body Adhesion" 1993, J. Neurosc. 13(11): 4764-4775.
Avrameas et al. "Polyreactive anti-DNA monoclonal antibodies and a derived peptide as vectors for the intracytoplasmic and intranuclear translocation of macromolecules" 1998, Proc. Natl. Acad. Sci. USA 95:5601-5606.
Banker et al. "Modern Pharmaceutics" 1979, Marcel Dekker, Inc. (TOC).
Banker et al. "Modern Pharmaceutics" 2002, 4$^{th}$ Ed., Informa Healthcare, New York (TOC).
Bao et al. "A Functional Dermatan Sulfate Epitope Containing Iduronate (2-O-sulfate) α1-3GalNAC (6-O-sulfate) Disaccharide in the Mouse Brain" 2005, J of Bio. Chem. 280(24):23184-23193.
Basso et al. "A Sensitive and Reliable Locomotor Rating Scale for Open Field Testing in Rats" 1995, J. of Neurotrama 12(1):1-21.
Ben-Bassat et al. "Processing of the Initiation Methionine from Proteins: Properties of the Escherichia coli Methionine Aminopeptidase and Its Gene Structure" 1987, J. Bacteriol. 169(2):751-757.
Bixby et al. "Neurite outgrowth on muscle cell surfaces involves extracellular matrix receptors as well as $Ca^{2+}$-dependent and -independent cell adhesion molecules" 1987, Proc. Natl. Acad. Sci. USA 84:2555-2559.
Blight et al. "Animal models of spinal cord injury" 2002, Top Spinal Cord Inj. Rehabi. 6(2):1-13.
Bowie et al. "Deciphering the Message in Protein Sequences: Tolerance to Amino Acid Substitutions" 1990, Science 247:1306-1319.
Bradbury et al. "Chondroitinase ABC Promotes Functional Recovery After Spinal Cord Injury" 2002, Nature 416:636-640.
Bradbury et al. "Chondroitinase ABC Promotes Regeneration and Functional Recovery Following Spinal Cord Injury" 2001, Soc. for Neuroscience Abstracts 27(2):1835.
Bradbury et al. "NT-3 Promotes Growth of Lesioned Adult Rat Sens Ory Axons Ascending in the Dorsal Columns of the Spinal Cord" 1999, Eur. J. Neurosc. 11(11):3873-3783.
Bray et al. "Neuronal and Nonneuronal Influences on Retinal Ganglion Cell Survival, Axonal Regrowth, and Connectivity after Axotomy" 1991, Ann. NY Acad. Sci., 214-228.
Broach et al. "Experimental Manipulation of Gene Expression" M. Inouye ed., Academic Press, New York, 1983, pp. 83-117.
Burgess et at "Possible Dissassociation of the Heparin-binding and Mitogenic Activities of Heparin-binding (Acidic Fibroblast) Growth Factor-1 From Its Receptor-binding Activities by Site-directed Mutagenesis of a Single Lysine Residue" 1990, J. of Cell. Bio. 111:2129-2138.
Cadelli et al. "Oligodendrocyte- and Myelin-Associated Inhibitors of Neurite Outgrowth: Their Involvement in the Lack of CNS Regeneration" 1992, Exp. Neur. 115:189-192.
Caggiano et al., Chondroitinase ABCI Improves Locomotion and Bladder Function following Contusion Injury of the Rat Spinal Cord, Feb. 1, 2005, J. Neurotrauma 22(2):226-239.
Cajal "Degeneration & Regeneration of the Nervous System" May 1959 ed., Hafner Publ. Co., New York (TOC).
Chang et al. "Extension of Neurites on Axons is Impaired by Antibodies against Specific Neural Cell Surface Glycoproteins" 1987, J. Cell. Biol. 104:355-362.
Chau et al. "Chondroitinase ABC Enhances Axonal Regrowth Through Schwann Cell-seeded Guidance Channels After Spinal Cord Injury" Nov. 20, 2003 FASEB J. 18(1):1-24.
Chen et al. "Peripheral nerve regeneration using silicone rubber chambers filled with collagen, laminin and fibronectin" 2000, Biomat. 21:1541-1547.
Crespo et al. "How Does Chondroitinase Promote Functional Recovery in the Damaged CNS?" 2007, Ex. Neurology 206:159-171.
Curinga et al. "Mammalian-produced Chondroitinase AC Mitigates Axon Inhibition by Chondroitin Sulfate Proteoglycans" 2007, J. of Neurochemistry 102:275-288.
Daichi "Text Book of Physiology" 2000, 3$^{rd}$ 81.

(56) References Cited

OTHER PUBLICATIONS

Definition of "contusion" found in Medline Plus Dictionary (retrieved from website http://www.merriam-webster.com/dictionary/contusion on Sep. 11, 2011).
Definition of "crush injury" found in Medline Plus Dictionary (retrieved from website http://www.nlm.nih.gov/medlineplplus/ency/article/000024.htm on Sep. 11, 2011).
Degrendele et al "Requirement for CD44 in Activated T Cell Extravassation into an Inflammatory Site" 1997, *Science* 278:672-675.
Denuziere et al. "Chitosan-Chondroitin sulfate and chitosan-hyaluronate polyelectrolyte complexes: biological properties" 1998, *Biomaterials* 19:1275-1285.
Derossi et al. "Cell Internalization of the Third Helix of the Antennapedia Homeodomain is Receptorindependent" 1996, *J. Biol. Chern* 271:18188-18193.
Dimayuga et al. "The Neuregulin GGF2 Attenuates Free Radical Release from Activated Microglial Cells" Mar. 2003, *J. Neuroim.* 136(1-2):67-74.
Doppenberg et al. "Clinical Trials in Traumatic Brain Injury" 1998, *Ann. NY Acad. Sci.* 305-319.
Edelman "Cell Adhesion Molecules" 1983, *Science* 219:450-457.
Edelman et al. "Morphoregulatory Molecules" 1990, Wiley, New York (TOC).
Efthymiadis et al. "The HIV-1 Tat Nuclear Localization Sequence Confers Novel Nuclear Import Properties" Jan. 16, 1998, J. *Biol. Chern.* 273(3):1623-1628.
Ellioit et al. "Intercellular Trafficking and Protein Delivery by a Herpesvirus Structural Protein" 1997, *Cell* 88:223-233.
European Search Report and Written Opinion for EP04752310 dated Oct. 7, 2008.
European Search Report and Written Opinion for EP06815505 dated Feb. 22, 2010.
European Search Report and Written Opinion for EP10183555 dated Jan. 20, 2011.
European Search Report and Written Opinion for EP10184697 dated Jul. 12, 2011.
European Search Report and Written Opinion for EP11152626 dated Jul. 21, 2011.
Fahraeus et al. "Inhibition of pRb phosphorylation and cell-cycle progression by a 20-residue peptide derived from p16CDKN2IINK4A" 1996, *Curr. Biol.* 6(1):84-91.
Favre et al. "Hyaluronidase enhances recombinant adeno-associated virus (Raav)-mediated gene transfer in the rat skeletal muscle" 2000, Gene Ther. 7(16):1417-1420.
Fawcett et al. "The glial scar and central nervous system repair" 1999, *Brain Res. Bull.* 49(6):377-391.
Fawell et al. "Tat-mediated delivery of heterologous proteins into cells" 1994, *Proc. Natl. Acad. Sci. USA* 91:664-668.
Fethiere et al. "Crystal Structure of Chondroitin Ac Lyase, a Representative of a family of Glycosaminoglycan Degrading Enzymes" 1999, *J. Mol. Biol.* 288:635-647.
Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.
Frankel et al. "Tat Protein from Human Immunodeficiency Virus Forms a Metal-Linked Dimer" 1988, *Science* 240:70-73.
Frankish et al. "Spinal-cord Repair Moves a Step Closer" 2002, *The Lancet* 359(9314):1317.
Gennaro "Remington's Pharmaceutical Sciences" 1985, Mack Publishing Company (PA) 17$^{th}$ Ed. (TOC).
Goodman et al. "The Pharmacological Basis of Therapeutics" 1980, 6$^{th}$ ed., MacMillan Pub., New York (TOC).
Goodman et al. "The Pharmacological Basis of Therapeutics" 2001, 10$^{th}$ ed., McGraw Hill, New York (TOC).
Grandpre et al. "Nogo-66 Receptor Antagonist Peptide Promotes Axonal Regeneration" May 30, 2002, *Nature* 417(6888):547-551.
Hamai et al. "Two Distinct Chondroitin Sulfate ABC Lyases" 1997, *J. Biol. Chem.* 272(14):9123-9130.

Hirschberg et al. "Inflammation after axonal injury has conflicting consequences for recovery of function: rescue of spared axons is impaired but regeneration is supported" 1994, *J. Neuroimmunol.* 50(1):9-16 (Abstract).
Hiyama et al. "Crystallization and Some Properties of Chondroitinase from Arthrobacter Aurescens" 1975, *J. Biol. Chem.* 250:1824-1828.
Hlavin et al. "Molecular Structure and Functional Testing of Human L1CAM: An Interspecies Comparison" 1991, *Genomics* 11:416-423.
Hoffman et al. "Chondroitin Sulfates" 1958, *Federation Proc.* 17:1078-1082.
Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.
Hou et al. "Endotoxin Removal by Anion-Exchange Polymeric Matrix" 1990, *Biotech. Appl. Biochem.* 12:315-324.
Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.
Huang et al. "Crystal Structure of Chondroitinase B from Flavobacterium heparinum and its Complex with a Disaccharide Product at 107 A Resolution" 1999, *J. Mol. Biol.* 294:1257-1269.
Huang et al. "Crystal Structure of *Proteus vulgaris* Chondroitin Sulfate ABC Lyase I at 1.9 A Resolution" May 2, 2003, *J. Mol. Biol.* 328(3):623-634.
Hunt et al. "The Nogo Receptor, Its Ligands and Axonal Regeneration in the Spinal Cord; a Review" Feb. 2002, *J. Neurocytology* 31(2):93-120.
Iida et al. "Cell Surface Chondroitin Sulfate Proteoglycans in Tumor Cell Adhesion, Motility and Invastion" 1996, *Seminars in Cancer Biology* 7:155-162.
Iwai et al. "Axon Patterning Requires *DN*-cadherin, a Novel Neuronal Adhesion Receptor, in the *Drosphila* Embryonic CNS" 1997, Neuron 19:77-89.
Jones "Taking a new TAK on Tat transactivation" 1997, *Genes & Dev.* 11:2593-2599.
Jung et al. "Transit time of leutocytes rolling through venules controls cytokine-induced inflammatory cell recruitment in vivo" 1998, *J. Clin. Invest.* 102(8):1526-1533.
Kadmon et al. "Functional Cooperation between the Neural Adhesion Molecules L1 and N-CAM is Carbohydrate Dependent" 1990, *J. Cell Biol.* 110:209-218.
Kadmon et al. "The Neural Cell Adhesion Molecule N-CAM Enhances L1-dependent Cell-Cell Interactions" 1990, *J. Cell Biol.* 110:193-208.
Khan et al. "Animal Models of Spinal Cord Contusion Injuries" 1999, Laboratory Animal Science 49(2): 161-172.
Kim et al. "Insertion and Deletion Mutants of *Fok*I Restriction Endonuclease" 1994, *J. Biol.Chem.* 269(50):31978-31982.
Korn "The Degradation of Heparin by Bacterial Enzymes" 1957, *J. Biol. Chem.* 226:841-844.
Krekoski et al. "Axonal Regeneration into Acellular Nerve Grafts is Enhanced by Degradation of Chondroitin Sulfate Proteoglycan" 2001, *J. Neurosci.* 15:21(16):6206-6213.
Kubota et al. "Functional Similarity of HIV-1 Rev and HTLV-1 Rex Proteins: Identification of a New Nucleolar-Targeting Signal in Rev Protein" Aug. 15, 1989, *Biochem. Biophys. Res. Commun.* 162(3):963-970.
Kwon et al. "Animal Models Used in Spinal Cord Regeneration Research" 2002, *Spine* 27(14):1504-1510.
Lagenaur et al. "An L1-like molecule, the 8D9 antigen, is a potent substrate for neurite extension" 1987, *Proc. Natl. Acad. Sci. USA* 84:7753-7757.
Lemons et al. "Chondroitin Sulfate Preteoglycan Immunoreactivity Increases Following Spinal Cord Injury and Transplantation" 1999, *Exper. Neurology* 160:51-65.
Lesley et al. "Variant Cell Lines Selected for Alterations in the Function of the Hyaluronan Receptor CD44 Show Differences in Glycosylation" 1995, *J. Exp. Med.* 182:431-437.

(56) References Cited

OTHER PUBLICATIONS

Li et al. "Delayed systemic Nogo-66 Receptor Antagonist Promotes Recovery from Spinal Cord Injury" 2003, *J. Neuroscience* 23(10):4219-4227.
Lindholt et al. "A Single Mutation Affects Both N-acetylglucosaminOtransferase and Glucuronosyltransferase Activities in a Chinese Hamster Ovary Cell Mutant Defective in Heparan Sulfate Biosynthesis" Mar. 1992, *PNAS USA* 89:2267-2271.
Lindner et al. "L1 mono- and polyclonal antibodies modify cell migration in early postnatal mouse cerebellum" 1983, *Nature* 305:427-430.
Lodish et al. "Integrating cells into tissue" 2000, Mol. Cell Biology, $5^{th}$ Ed., Chapter 6.
Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.
Maniatis et al. "Molecular Cloning: A Laboratory Manual" 1982, Cold Spring Harbor Lab. (TOC).
Mann et al. "Endocytosis and Targeting of Exogenous HIV-1 Tat Protein" Jul. 10, 1991, *EMBO J.* (7):1733-1739.
Martinez et al. "Purification and Properties of the Enzyme Chondroitinase" 1959, *J. Biol. Chem.* 234(9):2236-2239.
Martini et al. "Restricted Localization of L1 and N-CAM Sites of Contact Between Schwann Cells and Neurites in Culture" 1994, *GLIA* 10:70-74.
Matinysn "Restoration of functions due to Enzyme Therepy After Complete Transaction of the Spinal Cord" 1965, *ZH EK SP KLIN MED* 5(3):3-13.
Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.
Matteuci et al. "Synthesis of Deoxyoligonucleotides on a Polymer Support" 1981, *J. Am. Chem. Soc.* 103:3185-3191.
McGee et al. "The Nogo-66 Receptor:Focusing Myelin Inhibition of Axon Regeneration" Apr. 2003, *Trends in Neuroscience* 26(4):193-198 XP004418152.
Michelacci et al. "A Comparative Study Between a Chondroitinase B and a Chondroitinase AC from *Flavobacterium heparinum*" 1975, *Biochem. J.* 151:121-129.
Michelacci et al. "Chondroitinase C from *Flavobacterium haparinum*" 1976, *J. Biol. Chem.* 251(4):1154-1158.
Michelacci et al. "Isolation and characterization of an induced Chondroitinase ABC" 1987, *Biochem. Biophys. Acta* 923:291-301.
Michelacci et al. "Isolation and Partial Characterization of an Induced Chondroitinase β from Flavobacterium Heparium" 1974, *Biochem. & Biophys. Res. Comm.* 56(4):973-980.
Miller et al. "N-terminal methionine-specific peptidase in *Salmonella typhimurium*" 1987, *PNAS* 84:2718-2722.
Miura et al. "Analysis of Glycosaminoglycan-Degrading Enzymes by Substrate Gel Electrophoresis (Zymography)" 1995, *Anal. Biochem.* 225:333-340.
Modena et al. "Hylauronidase-injectable microparticles intended for the treatment of extravasation" 1998, *J. Microencapsulation* 15(1):85-92.
Moon et al. "Regeneration of CNS axons back to their target following treatment of adult rat brain with chondroitinase ABC" 2001, *Nature Neurosc.* 4(5): 465-466.
Moos et al. "Neural adhesion molecule L1 as a member of the immunoglobulin superfamily with binding domains similar to fibronectin" 1988, *Nature* 334:701-703.
Nagahara et al. "Transduction of fUll-length TAT fusion proteins into mammalian cells: TAT_p27K1p1 induces cell migration" 1998, *Nat. Med.* 4(12):1449-1452.
Netti et al. "Role of Extracellular Matrix Assembly in Interstitial Transport in Solid Tumors" 2000, *Cancer Res.* 60(9):2497-2503.
Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.
Oermann et al. "The Use of Anti-inflammatory Medications in Cystic Fibrosis" 1999, *Chest* 115:1053-1058.
Olmarker et al. "Chondroitinase ABC (Pharmaceutical Grade) for Chemonucleolysis" 1996, *Spine* 21(17):1952-1956.
Onifer et al. "Rat Models of Traumatic Spinal Cord Injury to Assess Motor Recovery" 2007, *ILAR J.* 48(4):385-395.
Pawson et al. "Assembly of Cell Regulatory systems Through Protein Interaction Domains" 2003, *Science* 300:445-452.
Pillwein et al. "Hyaluronidase Additional to Standard Chemotherapy Improves Outcome for Children with Malignant Tumors" 1998, *Cancer Letters* 131:101-108.
Pojasek et al. "Biochemical Characterization of the Chondroitinase B Active Site" Aug. 23, 2002, *J. Biol. Chem.* 277(34):31179-31186.
Pojasek et al. "Recombinant Expression, Purification, and Kinetic Characterization of Chondroitinase AC and Chondroitinase B from Flavobacterium heparinum" 2001, *Biochem, Biophys. Res. Commun.* 286:343-351.
Prabhakar et al. "Biochemical Characterization of the Chondroitinase ABC I Active Site" Aug. 23, 2005, *Biochem. J.* 390(2):395-405.
Priestley et al. "Stimulating regeneration in the damaged spinal cord" 2002, *J. Phyl.* 96:123-133.
Rathjen et al. "Immunocytological and biochemical characterization of a new neuronal cell surface component (L1 antigen) which is involved in cell adhesion" 1984, *EMBO J.* 3(1):1-10.
Ratjen et al. "Cystic Fibrosis" 2003, The Lancet 361(9358):681-689 (Presentation).
Reich et al. "Small interfering RNA (siRNA) targeting VEGF effectively inhibits ocular neovascularization in a mouse model" 2003, *Molecular Vision* 9:210-216 (Abstract).
Reid et al. "Variants of Human L1 Cell Adhesion Molecule Arise through Alternate Splicing of RNA" 1992, *J. Mol. Neurosc.* 3:127-135.
Roy et al. "Generation of Substantially Smaller Deletion Mutants of Chondroitinase AC and B Those are Biologically Active" Nov. 8-12, 2003, Society for Neuroscience Abstract Viewer and Itinerary Planner, $33^{rd}$ Annual Meeting of the Society of Neuroscience, New Orleans, LA, Database Biosis, (Abstract).
Roy et al. "Treatment with Recombinant Chondroitinases AC and B Permits Neuronal Outgrowth Over Inhibitory Chondroitin Sulfate Proteoglycans (CSPGs)" Nov. 2, 2002, Society for Neuroscience Abstract Archives 2000-2005 (Abstract).
Saito et al. "Enzymatic Methods for the Determination of Small Quantities of Isomeric Chondroitin Sulfates" 1968, *J. Biol. Chem.* 243(7):1536-1542.
Sambrook et al. "Molecular Cloning" 1989, $2^{nd}$ ed., Cold Spring Harbor Laboratory Press, Ch. 16 and 17.
Sambrook et al. "Molecular Cloning" 1989, $2^{nd}$ ed., Cold Spring Harbor Laboratory Press, TOC.
Sato et al. "Cloning and expression in *Escherichia coli* of the gene encoding the Proteus vulgaris chondroitin ABC-lyase" Jan. 1, 1994, *Appl. Microbiol. Biotechnol.* 41:39-46.
Sato, et al. "Subunit Structure of Chondroitinase ABC from Proteus Vulgaris" 1986 *Agric. Biol. Chem.* 50(4):1057-1059.
Schachner "Functional implications of glial cell recognition molecules" 1990, *Neurosc.* 2:497-507.
Schwab "Nerve fibre regeneration after traumatic lesions of the CNS; progress and problems" 1991, *Phil. Trans. R. Soc. Lond.* 331:303-306.
Schwarze et al. "In Vivo Protein Transduction: Delivery of a Biologically Active Protein into the Mouse" 1999, *Science* 285:1569-1572.
Seikagaku Biobus. Corp. "Chondroitinase AC II pamphlet" 2009, URL: http//www.seikagakubb.co.jp/bio/cgi-bin/search/tenpu_pdf/100335.pdf.
Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Biol.* 107:341-351.

(56) References Cited

OTHER PUBLICATIONS

Silver et al. "Postnatally induced formation of the corpus callosum in acallosal mice on glia-coated cellulose bridges" 1983, *Science* 220:1067-1069.

Smiseth et al. "Effect of Hyaluronidase on Substrate Exchange and Blood Flow in the Ischaemic Myocardium of the Dog" 1982, *Clinical Physiology* 2(1):39-50.

Smith-Thomas et al. "Increased Axon Regeneration in Astrocytes Grown in the Presence of Proteoglycan Synthesis Inhibitors" 1995, *J. of Cell Science* 108(3):1307-1315.

Southern "Detection of Specific Sequences Among DNA Fragments Separated by Gel Electrophoresis" 1975, *J. Mol. Biol.* 98:503-517.

Stedman's Medical Dictionary 2000, Lippincott Williams & Wilkins, 27th Ed.

Sterne et al. "Neurotrophin-3 Delivered Locally via Fibronectin Mats Enhances Peripheral Nerve Regeneration" 1997, *Eur. J. Neurosc.* 9:1388-1396.

Tona et al. "Effect of Hyaluronidase on Brain Extracellular Matrix in Vivo and Optic Nerve Regeneration" 1993, *J. Neurosc. Res.* 36:191-199.

Trigg et al. "Peripheral Nerve Regeneration: Comparison of Laminin and Acidic Fibroblast Growth Factor" 1998, *Am. J Oto-laryngology* 19(1):29-32.

Tsuda et at "Substrate Specificity Studies of Flavobacterium Chondroitinase C and Heparitinases Towards the Glycosaminoglycan-protein Linkage region" 1999, *European J. of Biochem.* 262:127-133.

Vives et al. "A Truncated HIV-1 Tat Protein Basic Domain Rapidly Translocates through the Plasma Membrane and Accumulates in the Cell Nucleus" 1997, *J. Biol. Chem.* 272(25):16010-16017.

Vives et al. "Effects of the Tat Basic Domain on Human Immunodeficiency Virus Type 1 Transactivation, Using Chemically Synthesized Tat Protein and Tat Peptides" May 1994, *J. Virol.* 68(5):3343-3353.

Williams et al. "Calcium Influx into Neurons Can Solely Account for Cell Contact-dependent Neurite Outgrowth Stimulated by Transfected L1" 1992, *J. Cell Biol.* 119(4):883-892.

Wood et at "Inhibition of Schwann Cell Myelination in vitro by Antibody to the L1 Adhesion Molecule" 1990, *J. Neurosc.* 10(11):3635-3645.

Yamagata et al. "Purification and Properties of Bacterial Chondroitinases and Chondrosulfatases" 1968, *J. Biol. Chem.* 243(7):1523-1535.

Yamagata et al. "Repression of a Malignant Cell-Substratum Adhesion Phenotype by Inhibiting the Production of the Anti-Adhesive Proteoglycan, PG-M/Versican" 1994, *J. of Cell Science* 1007:2581-2590.

Yang et al. "Developmental Regulation of a Matrix Metalloproteinase during Regeneration of Axolotl Appendages" 1994, *Dev. Biol.* 166:696-703.

Yang et al. "Expression of *Mmp-9* and Related Matrix Metalloproteinase Genes During Axolotl Limb Regeneration" 1999, *Dev. Dyn.* 216:2-9.

Yasuda et al. "Effect of Hyluronidase on Experimental Cerebral Infarct Size and Mortality" 1982, *Lab. Invest.* 46(4):400-404.

Yick et al. "Chondroitinase ABC promotes axonal regeneration of Clarke's neurons after spinal cord injury" 2000, *Regeneration and Transpl.* 11(5):1063-1067.

Yick et al. "Chondroitinase ABC Promotes Axonal Regrowth of Clarke's Neurons Into Peripheral Nerve Graft After Hemisection of the Spinal Cord" 1999, Soc. for Neuroscience Abstracts 25:747.

Zuo et al. "Degradation of Chondroitin Sulfate Proteoglycan Enhances the Neurite-Promoting Potential of Spinal Cord Tissue" 1998, *Exp. Neurol.* 154(2):654-662.

Zuo et al. "Regeneration of Axons After Nerve Transection Repair is Enhanced by Degradation of Chondroitin Sulfate Proteoglycan" 2002, *Exp. Neurology* 176:221-228.

Csoka et al. "Purification and Microsequencing of Hyaluronidase Isozymes from Human Urine" 1997, FEBS Letters 307-310.

Fawcett et al. "Factors Influencing the Regeneration of Axons in the Central Nervous System" 1991, Paraplegia 287-293.

Horner et al. "Regenerating the Damaged Central Nervous System" Oct. 26, 2000, Nature 407:963-970.

Moon et al. "Limited Growth of Severed CNS Axons After Treatment of Adult Rat Brain with Hyaluronidase" 2003, J. Neuroscience Res. 71:23-37.

Schwarze et al. "In Vivo Protein Transduction: Intracellular Delivery of Biologically Active Proteins, Compounds and DNA" Feb. 2000, Trends Pharmcol. Sci. 21:45-58.

COMPOSITIONS AND METHODS FOR PROMOTING NEURONAL OUTGROWTH

CROSS-REFERENCE TO RELATED APPLICATIONS

This application is a continuation application of U.S. application Ser. No. 14/317,106, with a filing date of Jun. 27, 2014, which is a continuation application of U.S. application Ser. No. 13/451,968, filed on Apr. 20, 2012, now U.S. Pat. No. 8,785,606, issued Jul. 22, 2014 which is a continuation application of U.S. application Ser. No. 10/513,573, filed on Mar. 7, 2006, now U.S. Pat. No. 8,183,350, issued May 22, 2012 which is a national phase application filed under 35 U.S.C. § 371 of International Appln. No. PCT/US2003/014156, filed May 5, 2003, which claims priority to U.S. Provisional Appln. No. 60/377,669, filed May 4, 2002, the contents of each being incorporated by reference as if set forth in their entirely herein

BACKGROUND

Technical Field

This disclosure relates to methods for promoting neurite outgrowth after nerve cell loss as a result of central nervous system ("CNS") injury or disease. In particular, chondroitinase AC and chondroitinase B are used to promote neurite outgrowth.

Description of Related Art

After a spinal cord injury in the adult mammalian central nervous system (CNS), the inability of axons to regenerate may lead to permanent paralysis. An injury-caused lesion will develop glial scarring, which contains extracellular matrix molecules including chondroitin sulfate proteoglycans (CSPGs). CSPGs inhibit nerve tissue growth in vitro, and nerve tissue regeneration at CSPGs rich regions in vivo.

A number of molecules, and specified regions thereof, have been implicated in the ability to support the sprouting of neurites from a neuronal cell, a process also referred to as neurite outgrowth. The term neurite refers to both axon and dendrite structures. This process of spouting neurites is essential in neural development and regeneration, especially after physical injury or disease has damaged neuronal cells. Neurites elongate profusely during development both in the central and peripheral nervous systems of all animal species. This phenomenon pertains to both axons and dendrites. However, adult neurite regrowth in the CNS is increasingly lost with evolutionary progress.

Various polypeptides, especially cell adhesion molecules (CAMs), have been known to promote neural cell growth. While early efforts in this area of research concentrated on the adhesion-promoting extracellular matrix protein fibronectin (FN), other polypeptides have also been found to promote neural growth. For example, U.S. Pat. No. 5,792,743, discloses novel polypeptides and methods for promoting neural growth in the central nervous system of a mammal by administering a soluble neural CAM, a fragment thereof, or a Fc-fusion product thereof. U.S. Pat. No. 6,313,265 discloses synthetic polypeptides containing the pharmacologically active regions of CAMs that can be used in promoting nerve regeneration and repair in both peripheral nerve injuries as well as lesions in the central nervous system.

While helpful, the use of regenerative proteins alone may not be sufficient to effect repair of a damaged nervous system.

One area that has been determined to be of significance in the repair and regeneration of cellular tissue, including neural tissue, is the extracellular matrix. Extracellular matrix proteins ("EMPs") are found in spaces around or near cells of multicellular organisms and are typically fibrous proteins of two functional types: mainly structural, e.g., collagen and elastin, and mainly adhesive, e.g., fibronectin and laminin.

During approximately the past two decades, the base knowledge of cell adhesion and migration in extracellular matrices (ECMs) at the molecular level has expanded rapidly. The action of enzymes and other polypeptides which degrade components of the extracellular matrix and basement membranes may facilitate the events of neural repair by a variety of mechanisms including the release of bound cytokines and by increasing the permeability of the matrix, thereby enhancing the mobility of mediator molecules, growth factors and chemotactic agents, as well as the cells involved in the healing process. For example, U.S. Pat. No. 5,997,863 discloses the use of glycosaminoglycans to manipulate cell proliferation and promote wound healing.

ECM molecules include the inhibitory CSPGs. Components of the CSPGs have been identified as the glycosaminoglycans, chondroitin sulfate (CS) and dermatan sulfate (DS). Removal of these inhibitory molecules would allow neurites to regenerate and reinnervate an area after physical injury or disease.

Previous studies have found that chondroitinases can lyase and degrade CSPGs and, including, CS and DS. One study found that chondroitinase ABC removed glycosaminoglycan (GAG) chains in and around lesioned areas of rat CNS, in vivo. The degradation of GAGs promoted expression of a growth-associated protein, GAP-43, indicating increased regenerative propensity in treated cells. However, this growth-associated protein is associated with regeneration in peripheral, but not central, nerve injuries. Applications of chondroitinase ABC to an injured corticospinal tract (CST) prevented axon retraction from the affected area and promoted more axon fiber growth than the control, with some axons arborizing into gray matter. Regenerated CST axons established functional connections. (Bradbury et al., Chondroitinase ABC promotes functional recovery after spinal cord injury, Nature 416: 636-640 (2002)). Another study found that in vitro chondroitinase ABC treatment of rat spinal cord regenerated neurons on a tissue section substrata. This study observed that degradation of CSPGs may promote the neuro-stimulatory effects of laminin. (Zuo et al. Degradation of chondroitin sulfate proteoglycan enhances the neurite-promoting potential of spinal cord tissue, Exp. Neural. 154(2): 654-62 (1998)). In a later study by same primary researcher, it was reported that injection of chondroitinase ABC at the site of nerve damage degraded CSPGs and increased the ingress of axonal sprouts into the basal laminae of the distal nerve segment, which may be by enabling more latitude in growth at the interface of coapted nerve. (Zuo et al. Regeneration of axons after nerve transaction repair is enhanced by degradation of chondroitin sulfate proteoglycan. Exp. Neural. 176(1): 221-8 (2002)). The same group of researchers also found chondroitinase ABC treatments regenerated axons on into acellular grafts at a much higher rate than the control grafts. (Krekoski et al., Axonal regeneration into acellular nerve grafts is enhanced by degradation of chondroitin sulfate proteoglycan. J. Neurosci. 15:21(16): 6206-13 (2001)).

The use of chondroitinase AC and chondroitinase B would be advantageous to promote neurite growth in mammals because these chondroitinases strongly promote neurite outgrowths directly in the CNS, itself, as well as in the peripheral nervous system.

SUMMARY

Neurite outgrowth is promoted by administering chondroitinase AC, chondroitinase B or a mixture thereof to an injured area of the central nervous system.

Various types of chondroitinase AC, and chondroitinase B can be administered to a mammal afflicted with a CNS injury, whether the injury is immediate or long-standing. The chondroitinase is administered in amount effective to degrade CSPGs and thereby promote neurite outgrowth.

The chondroitinases can be administered with a suitable pharmaceutical carrier. The administration can be topical, local or systemic.

The administration of chondroitinases AC and/or chondroitinase B and the resulting promotion of neural growth in accordance with this disclosure restores motor and sensory functions, to varying degrees, depending on the responsiveness of each individual.

DETAILED DESCRIPTION

The present disclosure is directed to a method of treatment for mammalian central nervous system injuries, typically caused by trauma or disease. In particular, Chondroitinase AC and chondroitinase B, individually and in combination, provide a therapeutic treatment for spinal cord injuries. The phrase "spinal cord injuries" as used herein includes disease and traumatic injuries, such as severing or crushing of neurons brought about by an auto accident, fall, knife or bullet wound, as well as other injuries. Practice of the present methods will confer clinical benefits to the treated mammal, providing clinically relevant improvements in at least one of the subject's motor coordination functions and sensory perception. Clinically relevant improvements can range from a detectable improvement to a complete restoration of an impaired or lost central nervous system.

After a spinal cord injury in the adult mammalian central nervous system (CNS), the inability of axons to regenerate may lead to permanent paralysis. The site of the CNS spinal cord injury develops a lesion or glial scar by an increase in the deposition of extracellular matrix molecules by astrocytes and oligodendrocytes at the site of injury. These extracellular matrix molecules include chondroitin sulfate proteoglycans (CSPGs), which are highly expressed in scarring areas. CSPGs inhibit nerve tissue growth in vitro, and nerve tissue regeneration at CSPGs rich regions in vivo. Chondroitin sulfates A, B and C are the predominant forms found in mammals. These chondroitins may be involved in modulation of various biological activities including cell differentiation, adhesion, enzymatic pathways, and hormone interactions. The presence of chondroitin sulfate proteoglycans is elevated in the later stages of cell growth in response to tissue and vessel damage.

The glycosaminoglycans (GAGs), chondroitin sulfate (CS) and dermatan sulfate (DS), are important components of CSPG. They are inhibitory molecules that contribute to the lack of regeneration of the CNS in adult mammals, by hindering axonal and neuritic growth. (However, CSPGs are important in neuronal guidance and patterning during development, rather than inhibition).

Glycosaminoglycans are unbranched polysaccharides consisting of alternating hexosamine and hexuronic residues which carry sulfate groups in different positions. The GAGs are typically divided into three families according to the composition of the disaccharide backbone. These are: heparin/heparan sulfate [HexA-GlcNAc(SO.sub.4)]; chondroitin sulfate [HexA-GalNAc]; and keratan sulfate [Gal-GlcNAc]. The chondroitin sulfate family includes seven sub-types designated unsulfated chondroitin sulfate, oversulfated chondroitin sulfate, and chondroitin sulfates A-E, which vary in the number and position of their sulfate functional groups. Chondroitin sulfate B is also referred to as dermatan sulfate, and it differs in that iduronic acid is the predominant residue in the alternative hexuronic acid position.

It has now been found that the chondroitin enzymes chondroitinase AC and chondroitinase B are useful in controlling and/or inhibiting the effects of chondroitin sulfates and in developing therapeutics for the treatment of disease states.

Chondroitinase AC and chondroitinase B are chondroitin lyase enzymes, which may be derived from various sources. Any chondroitinase AC or B may be used in the disclosure, including, but not limited to chondroitinase AC (derived from *Flavobacterium heparinum*; T. Yamagata, H. Saito, O. Habuchi, S. Suzuki, J. Biol. Chem., 243, 1523 (1968)); chondroitinase AC II (derived for *Arthobacter aurescens*; K. Hiyama, S. Okada, J. Biol. Chem., 250, 1824 (1975), K. Hiyama, S. Okada, J. Biochem. (Tokyo), 80, 1201 (1976)); chondroitinase AC III (derived from *Flavobacterium* sp. Hp 102; H. Miyazono, H. Kikuchi, K. Yoshida, K. Morikawa, K. Tokuyasu, Seikagaku, 61, 1023 (1989)); chondroitinase B (derived from *Flavobacterium heparinum*; Y. M. Michelaaci, C. P. Dietrich, Biochem. Biophys. Res. Commun., 56, 973 (1974), Y. M. Michelaaci, C. P. Dietrich, Biochem. J., 151, 121 (1975), K. Maeyama, A. Tawada, A. Ueno, K. Yoshida, Seikagaku, 57, 1189 (1985)); and chondroitinase B (derived from *Flavobacterium* sp. Hp 102; H. Miyazono, H. Kikuchi, K. Yoshida, K. Morikawa, K. Tokuyasu, Seikagaku, 61, 1023 (1989)). Suitable chondroitinase AC and chondroitinase B are commercially available from Seikagaku America, Falmouth, Mass., USA. Additionally, the enzymes may be produced by the methods disclosed in U.S. Pat. No. 6,093,563 by Bennett et al., the disclosure of which is incorporated herein.

Chondroitinase enzyme activity can be stabilized by the addition of excipients or by lyophilization. Stabilizers include carbohydrates, amino acids, fatty acids, and surfactants and are known to those skilled in the art. Examples include carbohydrate such as sucrose, lactose, mannitol, and dextran, proteins such as albumin and protamine, amino acids such as arginine, glycine, and threonine, surfactants such as TWEEN® and PLURONIC®, salts such as calcium chloride and sodium phosphate, and lipids such as fatty acids, phospholipids, and bile salts. The stabilizers are generally added to the protein in a ratio of 1:10 to 4:1, carbohydrate to protein, amino acids to protein, protein stabilizer to protein, and salts to protein; 1:1000 to 1:20, surfactant to protein; and 1:20 to 4:1, lipids to protein. Other stabilizers include high concentrations of ammonium sulfate, sodium acetate or sodium sulfate, based on comparative studies with heparinase activity. The stabilizing agents, preferably the ammonium sulfate or other similar salt, are added to the enzyme in a ratio of 0.1 to 4.0 mg ammonium sulfate/IU enzyme.

Chondroitinase may be administered topically, locally or systemically. Topical or local administration is preferable for greater control of application. The chondroitinases, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing agents, preservatives, anesthetics and the like. Specifically pharmaceutical carriers that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds.

Pharmaceutical carriers may also be used in combination, such as polyethylene glycol and/or sucrose, or polyoxyethylene sorbitan fatty acid esters, polyoxyethylene sorbitan monooleate (20 E. O.) is particularly preferred.

The treatment regimen according to the invention is carried out by a means of administering chondroitinase AC and/or chondroitinase B to the lesions of the injured area of the CNS. The mode of administration, the timing of administration and the dosage are carried out such that the functional recovery from impairment of the CNS is enhanced by the promotion of neurite outgrowth. The treatments of the present disclosure deliver an effective amount of chondroitinase AC and/or chondroitinase B to the injured site. The term "effective amount" means an amount sufficient to degrade the CSPGs of the lesioned area of the spinal cord. The effective amount of chondroitinase can be administered in a single dosage, two dosages or a plurality of dosages. In a preferred embodiment, the dosage is administered within 12 hours after injury, or as soon as is feasible. In another embodiment, the dosage is administered to an injured mammal in one, two or a plurality of dosages; such dosages would be dependant on the severity of the injury and the amount of CSPGs present in the glial scarring. Where a plurality of dosages is administered, they may be delivered on a daily, weekly, or bi-weekly basis. The delivery of the dosages may be by means of catheter or syringe. Alternatively, the treatment can be administered during surgery to allow direct application to the glial scar.

Once the chondroitinases are administered, the degradation of CSPGs removes the inhibitory molecules that block neurite outgrowth, and allow the regeneration of neurites into the affected area. The chondroitinase AC and chondroitinase B degrade CS and DS, respectively, resulting in unsaturated sulfated disaccharides. Chondroitinase AC cleaves CS at 1,4 glycosidic linkages between N-acetylgalactosamine and glucuronic acid in the polysaccharide backbone of CS. Cleavage occurs through beta-elimination in a random endolytic action pattern. Chondroitinase B cleaves the 1,4 galactosamine iduronic acid linkage in the polysaccharide backbone of DS. The cleavage of both CS and DS occurs through a beta-elimination process which differentiates these enzymatic mechanisms from mammalian GAG degrading enzymes.

The removal of CS and DS from the glial scar permits the regeneration of neurite outgrowths into the injured area.

The regeneration of the nerve cells in to the affected CNS area allows the return of motor and sensory function. Clinically relevant improvement will range from a detectable improvement to a complete restoration of an impaired or lost nervous function, varying with the individual patients and injuries.

Although preferred and other embodiments of the invention have been described herein, further embodiments may be perceived by those skilled in the art without departing from the scope of the invention as defined by the following claims.

What is claimed is:

1. A method of restoring motor and sensory functions in a subject having an injury to the central nervous system comprising administering a composition comprising an effective amount of chondroitinase AC, chondroitinase B, or a mixture thereof to the subject.

2. The method of claim 1, wherein administration is by topical, local, or systemic.

3. The method of claim 1, wherein the composition comprises chondroitinase AC.

4. The method of claim 3, wherein the chondroitinase AC is selected from the group consisting of chondroitinase AC, chondroitinase AC II and chondroitinase AC III.

5. The method of claim 1, wherein the composition comprises chondroitinase B.

6. The method of claim 1, wherein the composition comprises chondroitinase AC and chondroitinase B.

7. The method of claim 1, wherein the composition further comprises a pharmaceutically acceptable carrier.

8. The method of claim 2, wherein local administration is by a catheter, a syringe, or direct application to the injury.

9. The method of claim 1, wherein the composition is administered in multiple doses.

10. The method of claim 1, wherein the injury is spinal cord injury.

* * * * *